(12) United States Patent
Scherzer et al.

(10) Patent No.: US 6,531,567 B2
(45) Date of Patent: Mar. 11, 2003

(54) MANNICH BASES AND FURTHER COMPOUNDS BASED ON ALKYLDIPROPYLENETRIAMINES

(75) Inventors: Wolfgang Scherzer, Bergkamen (DE); Jörg Volle, Selm/Bork (DE)

(73) Assignee: Vantico GmbH & Co., Bergkamen (DE)

( * ) Notice: Subject to any disclaimer, the term of this patent is extended or adjusted under 35 U.S.C. 154(b) by 35 days.

(21) Appl. No.: 09/815,613

(22) Filed: Mar. 23, 2001

(65) Prior Publication Data

US 2001/0034409 A1 Oct. 25, 2001

(30) Foreign Application Priority Data

Mar. 24, 2000 (DE) .......................... 100 14 655

(51) Int. Cl.[7] ...................... C08G 14/073; C08G 59/50; C08L 63/02
(52) U.S. Cl. .................. 528/123; 525/504; 525/523; 528/150; 528/162
(58) Field of Search ................. 528/150, 158, 528/162, 123; 525/504, 523

(56) References Cited

U.S. PATENT DOCUMENTS

| | | | |
|---|---|---|---|
| 3,280,074 A | | 10/1966 | McCaleb et al. |
| 3,337,606 A | | 8/1967 | Floyd |
| 3,615,797 A | * | 10/1971 | Ohtsuka et al. ................. 94/20 |
| 4,491,654 A | | 1/1985 | Cummings |
| 4,997,912 A | * | 3/1991 | Wirtz et al. .................. 530/232 |
| 5,534,039 A | * | 7/1996 | Huang et al. .................. 44/367 |
| 6,180,593 B1 | * | 1/2001 | Fender et al. ................ 510/515 |

FOREIGN PATENT DOCUMENTS

| | | |
|---|---|---|
| BE | 669 493 | 12/1965 |
| EP | 735 070 A1 | 10/1996 |
| EP | 758 661 A2 | 2/1997 |
| JP | 5-140418 A2 * | 6/1993 |
| WO | WO 01/21679 A1 | 3/2001 |
| WO | WO 01/72869 A2 | 10/2001 |

OTHER PUBLICATIONS

Nucl. Med. Biol. 1993, 20(2), pp. 211–216 as abstract.

* cited by examiner

*Primary Examiner*—Robert E. L. Sellers
(74) *Attorney, Agent, or Firm*—Proskauer Rose LLP; Kristin Neuman, Esq.

(57) ABSTRACT

The invention relates to Mannich bases prepared using alkyldipropylenetriamines and to addition compounds (adducts) of alkyldipropylenetriamines with acrylonitrile and ethylene oxide or propylene oxide, and to products obtained therefrom by the further addition of epoxy compounds having on average at least one epoxy group per molecule, and to the use of such products as hardeners for curable epoxy resin systems.

5 Claims, No Drawings

MANNICH BASES AND FURTHER COMPOUNDS BASED ON ALKYLDIPROPYLENETRIAMINES

The present invention relates to Mannich bases prepared using alkyldipropylenetriamines and to addition compounds (adducts) of alkyldipropylenetriamines with acrylonitrile and ethylene oxide or propylene oxide, to the products obtained therefrom by the further addition of epoxy compounds having on average at least one epoxy group per molecule, and to the use of such products as hardeners for epoxy resins and finally to a method of producing cured products using such curable compositions.

Curable compositions based on amine curing agents and epoxy resins are used widely in industry to coat and treat metal and mineral substrates. There are used as amine curing agents especially aliphatic, cycloaliphatic or aromatic amines as well as polyaminoamides which may or may not contain imidazoline groups.

The mechanical and physical properties of the curable compositions based on those amines are sufficient for many applications.

In the field of coatings in particular, however, there is a demand for binder systems that are surface-tolerant, that is to say that exhibit good adhesion even to substrates that are difficult to coat, such as, for example, damp substrates or sheet metal that has not been pretreated, and that provide optimum protection of the substrate, for example protection against corrosion. There is also a demand for rapid onset of curing of the binder systems after application to the substrates also at low temperatures, for example in order to provide rapid loading capability or to enable overcoating.

For external applications in particular, a high degree of early water resistance of the as yet uncured film (e.g. by droplet formation at high relative atmospheric humidity) is an important criterion, as is low viscosity of the binder so that the binder can still be processed even at low temperatures. Low temperatures are understood to be temperatures of generally less than 15° C. Highly viscous Mannich bases based on polyamines and alkylphenols are therefore poorly suited to such external applications. Moreover, they have a high colour number and in many cases exhibit unsatisfactory adhesion to the substrates described hereinbefore and poor adhesion to subsequently applied surface-coatings.

As hardeners for epoxy resins that have relatively good corrosion protection and useful adhesion even to difficult substrates there are known polyaminoamides that generally contain imidazoline groups. Such compounds are prepared by condensation of generally unsaturated, long-chain fatty acids with polyethylenepolyamines. The disadvantage of such compounds is their high viscosity at low temperatures (less than 15° C.) and the slow rate of onset of cure and full cure. Such compounds also have relatively high colour numbers.

The problem of the present invention was accordingly to overcome those disadvantages.

The problem was solved by the provision of the alkyldipropylenetriamine-based compounds according to the invention and their adducts with epoxy compounds that contain on average at least one epoxy group per molecule.

Surprisingly it has been found that although, in their structure, the alkyidipropylenetriamine-based compounds according to the invention are similar to polyaminoamides which may or may not contain imidazoline, they have a markedly higher rate of onset of cure and full cure, especially at low temperatures of less than 15° C. Moreover, such compounds have in comparison significantly lower viscosity and colour number.

The invention relates to products comprising one or more compound(s) of formula (I)

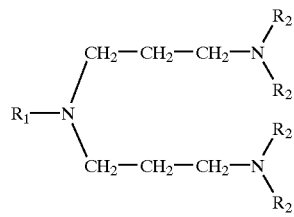

wherein $R_1$ is a hydrocarbon radical having from 8 to 22, preferably from 12 to 22, carbon atoms, and from 50 to 90 per cent of the $R_2$ radicals of the product denote a hydrogen atom and the remaining $R_2$ radicals of the product denote a group selected from a) a radical of formula

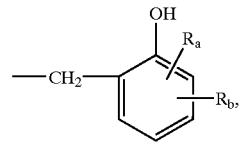

wherein $R_a$ and $R_b$ are each independently of the other a hydrogen atom or an aliphatic, cycloaliphatic, aromatic or araliphatic radical having from 1 to 22, preferably from 1 to 12, carbon atoms,
b) a radical of formula —$CH_2$—$CH(R_c)$—OH, wherein $R_c$ is —H or —$CH_3$, and
c) a radical of formula —$CH_2$—$CH_2$—CN.

The products accordingly comprise overall a composition of discrete compounds of formula 1, which may in theory have 0, 1, 2, 3 or 4 amine hydrogen atoms, the compounds having, however, as a statistical average over the total amount, from 50 to 90% amine hydrogen atoms.

Preference is given to products comprising more than one compound of formula (I), wherein from 60 to 85 per cent, preferably from 65 to 80 per cent, of the $R_2$ radicals of the product denote a hydrogen atom.

Preference is also given to products in the form of a compound of formula (I), wherein two or three, preferably three, of the $R_2$ radicals of the product denote a hydrogen atom.

As starting materials for the preparation of the products of general formula (I) according to the invention there are used alkyldipropylenetriamines of general formula (II)

wherein R is a hydrocarbon radical having from 8 to 22, preferably from 12 to 22, carbon atoms.

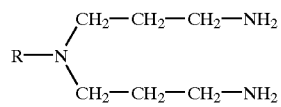

The compounds of formula (II) are customarily prepared by cyanoethylation of amines (fatty amines) and subsequent hydrogenation according to processes known per se.

In those processes the amines or fatty amines are reacted with acrylonitrile, and then the cyanide groups are hydrogenated in the presence of a catalyst. The reaction sequence can be shown schematically as follows:

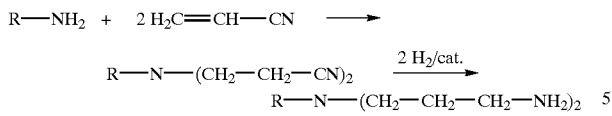

The so-called fatty amines preferably used as starting materials for the cyanoethylation are mixtures of long-chain primary alkylamines, obtained from mixed glycerol esters of medium and higher fatty acids having an even number of carbon atoms, as occur in plant and animal substances. For example, beef tallow contains almost 100% (esterified) fatty acids having a carbon chain length of 14, 16 and 18 carbon atoms. The beef tallow fatty amines obtained from beef tallow are commercially available as tallow fatty amine, e.g. Genamin® TA100 (Clariant). Accordingly, if fatty amines of natural products are used as starting materials in the preparation of amines according to formula (II), the products of general formula (II) comprise mixtures of compounds of different chain length R. The chains R have about from 8 to 20 carbon atoms, with a maximum of about 22 carbon atoms, and may either be saturated or have multiple bonds and may be either straight-chain or branched. Further examples of commercially available fatty amines that can be used according to the invention, in addition to tallow fatty amine, are saturated, straight-chain fatty amines, such as dodecylamine and tetradecylamine, saturated branched fatty amines, such as isotridecylamine, unsaturated and saturated fatty amines and fatty amine mixtures, such as coconut fatty amine, oleylamine, rape oil fatty amine and stearylamine.

The products of formula (I) wherein some of the $R_2$ radicals of the product denote hydrogen atoms and the remaining $R_2$ radicals of the product denote a radical of formula

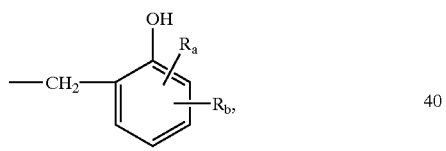

wherein $R_a$ and $R_b$ are each independently of the other a hydrogen atom or an aliphatic, cycloaliphatic, aromatic or araliphatic radical having from 1 to 22, preferably from 1 to 12, carbon atoms, are so-called Mannich bases. They are prepared in a manner known per se, for example by taking a compound of formula (II) and then adding a phenol derivative and dissolving it at elevated temperature. In the next step, paraformaldehyde in the form of granules is so added in portions that the temperature of the exothermic reaction does not exceed 100° C. Once the addition is complete, the reaction mixture is gradually heated to 150° C. over the course of one hour, with the reaction water that is formed being distilled off. The success and completion of the reaction can be monitored easily by reference to the amount of water collected. Other possible preparation methods include the complete or partial reaction of the phenol derivative with an aldehyde before adding the amine; also, first the reaction of amine and aldehyde before adding the phenol derivative; and finally the simultaneous controlled combination and reaction of all three starting materials. The molar ratios of the triamine and phenol derivative starting materials used are so selected that the resulting products still contain from 50 to 90, preferably from 60 to 85, especially from 65 to 80, per cent of the original hydrogen atoms of the two primary amines of the alkyldipropylenetriamine used. The molar ratios of the triamine and phenol derivative starting materials used can also be so selected that in the resulting product from 50 to 75%, corresponding to two or three, preferably three, of the $R_2$ radicals denote a hydrogen atom. Also used are Mannich bases from phenols in which 2 or 3 mol of the amine compound of general formula (II) are also added per mol of phenol component. In the case of phenol, for example, 1, 2 or 3 mol of the amine compound may be added, whereas, for example, in the case of ortho- or para-cresol only 1 or 2 mol of amine compound may be added and, for example, in the case of 2,6-dimethylphenol only 1 mol of amine compound may be added. The molar ratio of amine:aldehyde:phenol can thus be varied from 1:1:1 to 3:3:1. Preferably the aldehyde is used in an equimolar amount relative to the phenol. The aldehyde may also be used in excess according to the invention. Preference is in that case given to a maximum of 0.5 mol of aldehyde excess per mol of phenol.

As phenolic component there may be used any aromatic compound that has at least one hydroxy group bonded to at least one aromatic ring. The aromatic ring(s) may carry one or more radicals, such as, for example, an alkyl group. A mononuclear aromatic group can be illustrated by the formula

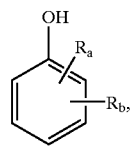

wherein $R_a$ and $R_b$ are each independently of the other a hydrogen atom or a radical having from 1 to 22 carbon atoms. The radical can be linear, branched or aromatic. Examples of mononuclear phenols include phenol, ortho-, meta- or para-cresol, isomeric xylenols, alkylphenols, such as n- or iso-butylphenol, octylphenol, nonylphenol and dodecylphenol.

Polyphenols that can be used include polynuclear phenols having at least two phenol units in the molecule, wherein hydrogen atoms must be present in the ortho- or para-position relative to the hydroxy group. Examples thereof include 4,4'-dihydroxydiphenyl, 4,4'-dihydroxydiphenyl ether, 4,4'-dihydroxydiphenylmethane, bisphenol A and 4,4'-dihydroxydiphenylsulfone, as well as the condensation products of phenol and formaldehyde termed novolaks. Preference is given to bisphenol A and bisphenol F.

The products comprising one or more compound(s) of formula (I)

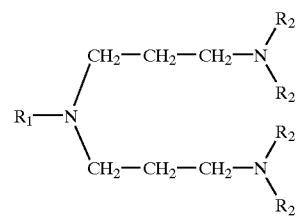

wherein some of the $R_2$ radicals of the product denote hydrogen atoms and the remaining $R_2$ radicals of the product denote a radical of formula —$CH_2$—$CH(R_c)$—OH, wherein $R_c$ is —H or —$CH_3$, are products of addition reactions (adducts). The adducts are prepared according to processes known per se, by taking a compound of formula (II) and then adding ethylene oxide and/or propylene oxide in liquid or gaseous form.

The molar ratios of the triamine and ethylene oxide or propylene oxide starting materials used are so selected that the resulting products still contain from 50 to 90, preferably from 60 to 85, especially from 65 to 80, per cent of the original hydrogen atoms of the two primary amines of the alkyldipropylenetriamine used. The molar ratios of the triamine and ethylene oxide or propylene oxide starting materials used can also be so selected that in the resulting product from 50 to 75%, corresponding to two or three, especially three, of the $R_2$ radicals denote a hydrogen atom.

The products comprising one or more compound(s) of formula (I)

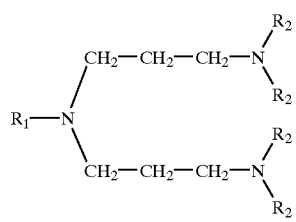

wherein some of the $R_2$ radicals of the product denote hydrogen atoms and the remaining $R_2$ radicals of the product denote a radical of formula —$CH_2$—$CH_2$—CN, are also products of addition reactions. Such products are prepared by taking a compound of formula (II) and then adding acrylonitrile over the course of one hour at slightly elevated temperature (about 30–45° C.). With subsequent stirring, the reaction mixture is then left to cool to room temperature. The molar ratios of the triamine and acrylonitrile starting materials used are so selected that the resulting products still contain from 50 to 90, preferably from 60 to 85, especially from 65 to 80, per cent of the original hydrogen atoms of the two primary amines of the alkyldipropylenetriamine used. The molar ratios of the triamine and acrylonitrile starting materials used can also be so selected that in the resulting product from 50 to 75%, corresponding to two or three, preferably three, of the $R_2$ radicals denote a hydrogen atom.

The present invention relates also to products obtainable by reacting a product comprising one or more compound(s) of formula (I), wherein $R_1$ is a hydrocarbon radical having from 8 to 22, preferably from 12 to 22, carbon atoms, and from 50 to 90 per cent of the $R_2$ radicals of the product denote a hydrogen atom and the remaining $R_2$ radicals of the product denote a group selected from a) a radical of formula

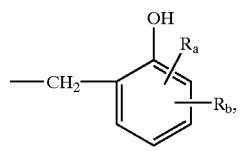

wherein $R_a$ and $R_b$ are each independently of the other a hydrogen atom or an aliphatic, cycloaliphatic, aromatic or araliphatic radical having from 1 to 22, preferably from 1 to 12, carbon atoms, b) a radical of formula —$CH_2$—$CH(R_c)$—OH, wherein $R_c$ is —H or —$CH_3$, and c) a radical of formula —$CH_2$—$CH_2$—CN, with an epoxy compound that contains on average at least one epoxy group per molecule, the amount of the epoxy compound being so selected that from 50 to 80 per cent of the $R_2$ radicals of the reaction product denote a hydrogen atom.

Preference is given to the use of products of formula (I) wherein $R_1$ is a hydrocarbon radical having from 12 to 22 carbon atoms and wherein from 60 to 85 per cent, preferably from 65 to 80 per cent, especially three, of the $R_2$ radicals denote a hydrogen atom.

The adducts according to the invention comprising epoxy compounds that contain on average at least one epoxy group per molecule are prepared according to known processes, wherein the epoxy compounds are added dropwise, advantageously at from 50° C. to 100° C., with stirring, to the alkyldipropylenetriamine derivatives according to general formula (I) used as starting material and described hereinabove, and the mixture is then stirred for about 30 minutes at the same temperature until the addition reaction is complete. The amount of epoxy compound used will be determined by taking into consideration the epoxy functionality of the epoxy compound on the one hand and the desired N-H functionality of the resulting adduct on the other hand. The desired N-H functionality should be two or greater than two.

The epoxy compounds used for the addition reaction of the above-mentioned products according to formula (I) are known commercially available products that have at least one epoxy group per molecule. According to the invention preference is given to glycidyl ethers based on mono- or poly-hydric phenols, such as, for example, phenol, cresol, bisphenol A, bisphenol F, novolaks, mono- or poly-hydric aliphatic alcohols having from 4 to 18 carbon atoms, such as, for example, butanol, butanediol, hexanol, hexanediol, fatty alcohols having a chain length of from 8 to 18 carbon atoms, polyoxyalkylene glycols, such as diethylene glycol, dipropylene glycol, polyoxypropylene glycol, polyoxyethylene glycols, diethylene glycol monobutyl ether, and epoxy compounds prepared by direct epoxidation, such as styrene oxide.

According to the invention it is possible to use as hardener for epoxy compounds any of the products described above in which the NH functionality is two or greater than two. Accordingly it is possible to use both the products comprising one or more compound(s) according to general formula (I) and the adducts derived from those products with epoxy compounds. It is also possible to use as hardener for epoxy compounds any possible combination of two or more of the alkyldipropylenetriamine derivatives described above.

The degree of addition can be varied within certain limits and is influenced on the one hand by the NH functionality of one of the amine compounds according to formula (I) used and on the other hand by the epoxy functionality of the epoxy compound used and can furthermore be selected in accordance with the particular field in which the curable composition is to be used.

Suitable results are generally obtained when from 0.1 to 1 mol of epoxy compound is used per mol of amine compound, so that on average there are more than two free amine hydrogen atoms in the resulting adduct.

The invention accordingly relates also to curable compositions comprising a) at least one product selected from the above-described products of formula (I) and the products obtained therefrom by further addition of epoxy compounds having on average at least one epoxy group per molecule, and b) at least one epoxy compound having on average more than one epoxy group in the molecule, and optionally c) modifiers, such as diluents and further customary adjuvants and additives.

The invention relates also to products that are obtainable by thermal curing of a curable composition according to the invention.

For the curable compositions according to the invention, it is also possible to use, in addition to the hardeners according to the invention, further known amine epoxy resin hardeners. The modifiers c) can be added equally to the hardener a), to the resin b), except for further curing agents, or to the curable composition.

The products a) according to the invention together with components c) are preferably adjusted to a preferred mixing ratio of 50–100 parts by weight of hardener per 100 g of epoxy resin b). Depending on the adjustment of the desired end properties, the mixing ratios may also be less than 50 parts by weight or more than 100 parts by weight of hardener per 100 g of resin b).

The amount of diluents should not exceed 40%, based on the hardener, since there is otherwise too great a deterioration in the mechanical properties.

The ratio of reactive groups of the products of general formula (I) according to the invention and/or adducts thereof and optionally additional amine curing agents to the epoxy groups of component b) is preferably equivalent. Again, however, depending on the adjustment of the desired properties, it is, in some cases, possible to depart quite considerably from equivalence, either above or below it.

As diluents there may be used both compounds that largely remain in the duromer after full curing, such as, for example, high boiling alcohols and ethers, such as benzyl alcohol, ethylene glycol, propylene glycol, butyl diglycol etc., and compounds that largely evaporate from the coating during curing, such as, for example, xylene, butanol, methoxypropanol and water.

In order to adjust the end properties, as additional amine component there can also be used any customary amines, for example polyethylenepolyamines, such as diethylenetriamine, triethylenetetramine, tetraethylenepentamine, etc.;

polypropylenepolyamines, such as dipropylenetriamine, tripropylenetetramine, and the polyamines obtained by cyanoethylation of polyamines, especially of ethylenediamine, and subsequent complete or partial hydrogenation;

aliphatic amines, such as diaminoethane, diaminopropane, neopentanediamine, diaminobutane, hexamethylenediamine, 2,2,4(2,4,4)-trimethylhexamethylenediamine-1,6;

cycloaliphatic polyamines, such as isophorone-diamine, diaminocyclohexane, norbornanediamine, 3(4),8(9)-bis(aminomethyl)tricyclo[5.2.1.0]decane, (TCD-diamine), 1,3-bis(aminomethyl)cyclohexane, bis(aminomethylcyclohexyl)methane;

heterocyclic polyamines, such as N-aminoethylpiperazine, 1,4-bis(aminopropyl) piperazine; araliphatic amines, such as xylylenediamine;

polyoxyalkylenepolyamines;

aromatic amines, such as diaminodiphenylmethane;

polyaminoamides which may or may not contain imidazoline, such as condensation products of mono- or di-meric fatty acids with polyethylenepolyamines.

The epoxy compounds co-used according to the invention are commercially available products having on average more than one epoxy group per molecule and that are derived from mono- and/or poly-hydric and/or polynuclear phenols, especially bisphenols and novolaks, such as diglycidyl ether of bisphenol A and diglycidyl ether of bisphenol F. A comprehensive list of such epoxy compounds can be found in the manual "Epoxid-verbindungen und Epoxidharze" by A. M. Paquin, Springer Verlag Berlin, 1958, Chapter IV, and in Lee & Neville, "Handbook of Epoxy Resins", 1967, Chapter 2.

It is also possible to use mixtures of two or more epoxy compounds. According to the invention, preference is given to mixtures of glycidyl ethers based on bisphenol A, bisphenol F or novolaks with so-called reactive diluents, such as monoglycidyl ethers of phenols or glycidyl ethers based on mono- or poly-hydric aliphatic or cycloaliphatic alcohols. Examples of such reactive diluents include, for example, phenyl glycidyl ether, cresyl glycidyl ether, p-tert-butylphenyl glycidyl ether, butyl glycidyl ether, $C_{12-14}$alcohol glycidyl ether, butanediol diglycidyl ether, hexanediol diglycidyl ether, cyclohexanedimethylol diglycidyl ether, and glycidyl ethers based on polyethylene or polypropylene glycols. If necessary, the viscosity of the epoxy resins can be further reduced by adding such reactive diluents.

It is also possible to add to the curable compositions according to the invention the customary adjuvants and additives, for example fillers, such as pyrites, sands, silicates, graphite, silicon dioxide, talcum, mica, etc., in the particle size distribution customary in that field, and also pigments, dyes, stabilisers, flow improvers/plasticisers, non-reactive extender resins and softeners. The amounts of adjuvants and additives used relative to the resin/hardener mixture will depend upon the desired intended use, and upon the prevailing conditions of use and the material properties to be obtained and will be known to the person skilled in the art.

Mannich bases based on polyamines and alkylphenols are highly viscous and have a high colour number. By contrast, the products of formula (I) according to the invention, termed Mannich bases, and also their adducts with epoxy compounds, surprisingly have very low viscosity and are light in colour. They also surprisingly exhibit rapid curing at low temperatures combined with a long pot life. The Mannich bases according to the invention also have a high degree of early water resistance. As a result of the combination of the properties mentioned, Mannich bases according to the invention are especially suitable for low-temperature curing in difficult climatic conditions.

Polyaminoamides derived, for example, from tetraethylenetetramine and fatty acid amines have high viscosity. Fatty amines are, in their structure, very similar to those products. By contrast, the products of formula (I), termed fatty amine alkoxylates, and their adducts with epoxy compounds, surprisingly have very low viscosity and are light in colour. Compared with polyaminoamideslimidazolines, the fatty amine alkoxylates according to the invention also have a markedly improved curing rate. Finally the compounds have a long pot life, good early water resistance and good adhesion to metal and mineral substrates. As a result of the combination of the properties mentioned, the fatty amine alkoxylates according to the invention are, for example, suitable as hardeners for epoxy resins in protecting surface-coatings and structures, even under difficult external conditions.

On the other hand, the nitrites of formula (I) according to the invention, thus the products of formula (I) wherein some of the $R_2$ radicals of the product denote hydrogen atoms and the remaining $R_2$ radicals of the product denote a radical of formula —$CH_2$—$CH_2$—CN, and also their adducts with epoxy compounds, in contrast to the structurally similar polyaminoamide/-imidazole adducts, surprisingly have very low viscosity and a good curing rate. The nitrites according to the invention also have a long pot life and, at temperatures of down to about 15° C., have good surface properties associated with excellent adhesion to a wide variety of substrates. They are accordingly suitable for use wherever surface-tolerant epoxy resin/hardener systems are desired.

A common feature of the products according to the invention is that, owing to their properties, they are especially suitable as hardeners for binder systems for which special properties are required because of difficult climatic conditions.

Methods of Analysis

Viscosity

Measured using a Haake RV 20 rotation viscosimeter according to the manufacturer's instructions.

Colour Number

Measured according to DIN 53 995 using a Lovibond colour-measuring apparatus (Gardner colour number, APHA colour number).

Amine Number

Measured according to DIN 16 945.

Tecam Value

Value for the gelling time, measured using a Tecam Gelation Timer GT3 (Techne, Cambridge, GB), at 23° C. and 50% relative atmospheric humidity. Sample mixture of resin and hardener and accelerator=250 g.

Shore D Hardness

Measured using a type 38009 apparatus (Karl Frank GmbH) on test samples of 30 mm diameter and 6 mm thickness after 1 day and after 2 days, and after 2 days' and 24 hours' storage at 70° C.

Early Water Resistance/Whitening of the Film When Subjected to Water

Sample preparation:

The calculated amounts of epoxy resin and amine hardener are weighed into the mixing vessel and mixed intensively with a spatula for about 2 minutes, without incorporating an excessive amount of air therein. Local inhomogeneities manifest themselves in the form of streaks and are to be avoided.

A 500 μm film-drawing frame (Erichsen) is placed on a glass plate that has been cleaned with acetone and then dried, approximately 15 g of the reactive mixture are introduced and drawn over the free surface evenly. The freshly coated glass plates are immediately laid out in the appropriate climate-controlled chambers, typically at a relative atmospheric humidity (A.) of about 95% at 23° C., and about 80% at 10° C.

For evaluation of the early water resistance, the glass plates are brought back into the test laboratory after 24 hours' curing.

For the test, evaluation values are awarded (following the model of DIN 53230):

0=no defect; up to 5=most serious defects.

For fine differentiation, for example in the case of comparison samples, gradations of 0.5 are also possible.

0.5 ml of completely deionised water is applied by means of a pipette to a site on each plate and dabbed dry using cellulose wadding after 60 minutes.

Evaluation is made of the extent of colouration/whitening of the film at the site to which water was applied.

EXAMPLES

Example 1 Mannich Base 392 g (about 1 mol) of N,N-bisaminopropyl tallow fatty amine, prepared by reacting tallow fatty amine (a mixture of saturated and unsaturated alkylamines having 14–20 carbon atoms) with acrylonitrile and subsequent hydrogenation of the cyanide groups, are placed in a reactor vessel. 94 g (1 mol) of phenol in solid form is added and dissolved at about 50° C.

30 g (1 mol) of granulated paraformaldehyde are then so added in portions that the reaction temperature does not exceed 100° C. After the addition is complete, the reaction mixture is heated up to 150° C. over the course of about one hour, during which the reaction water is distilled off. The distillate weighs 18 g.

Example 2

Mannich Base

Analogously to Example 1, the following are reacted: 392 g of N,N-bisaminopropyl tallow fatty amine, 108 g of o-cresol (1 mol) and 30 g (1 mol) of paraformaldehyde.

Example 3

Mannich Base

Analogously to Example 1, the following are reacted: 392 g of N,N-bisaminopropyl tallow fatty amine, 114 g of bisphenol F (0.5 mol) and 30 g (1 mol) of paraformaldehyde.

Example 4

Mannich Base

Analogously to Example 1, the following are reacted: 392 g of N,N-bisaminopropyl tallow fatty amine, 94 g of phenol (1 mol) and 35 g (1.17 mol) of paraformaldehyde.

Example 5

Mannich base

Analogously to Example 1, the following are reacted: 392 g of N,N-bisaminopropyl tallow fatty amine, 113 g of phenol (1.2 mol) and 39 g (1.3 mol) of paraformaldehyde.

Example 6

Mannich Base

Analogously to Example 1, the following are reacted: 299 g of N,N-bisaminopropyidodecylamine (about 1 mol), 94 g of phenol and 30 g (1 mol) of paraformaldehyde.

Example 7

Mannich Base Adduct 90 g (about 0.18 mol) of the Mannich base according to Example 1 are taken and heated to 80° C. 10 g of cresyl glycidyl ether (0.06 mol) are added with continuous stirring. When the addition is complete, stirring is maintained for a further one hour.

Example 8

Mannich Base+plasticiser 90 g of the Mannich base according to Example 1 and 10 g of benzyl alcohol are homogenised at about 40° C.

Example 9

ACN Adduct+plasticiser 392 g (about 1 mol) of N,N-bisaminopropyl tallow fatty amine are placed in a reactor vessel. After heating to about 30° C., 53 g of acrylonitrile (ACN, 1 mol) are added continuously over the course of one hour. The adduct is then left to cool to room temperature, and 111 g of benzyl alcohol are then stirred in.

Example 10

ACN Adduct+plasticiser

Analogously to Example 9, the following are reacted: 299 g of N,N-bisaminopropyidodecylamine (about 1 mol), 53 g of acrylonitrile (1 mol) and 100 g of benzyl alcohol.

Example 11

ACN adduct+plasticiser

Analogously to Example 9, the following are reacted: 392 g of N,N-bisaminopropyl tallow fatty amine, 26.5 g of acrylonitrile (0.5 mol) and 100 g of benzyl alcohol.

Example 12

ACN Adduct+plasticiser

Analogously to Example 9, the following are reacted: 299 g of N,N-bisaminopropyldodecylamine (about 1 mol), 63.6 g of acrylonitrile (1.2 mol) and 100 g of benzyl alcohol.

Example 13

ACN Adduct+epoxide+plasticiser 80 g of the acrylonitrile adduct according to Example 11 are placed in a reactor vessel and homogenised with 10 g of benzyl alcohol. After heating to about 70° C., 10 g of a diglycidyl ether of bisphenol A (ep: 0.54) are added continuously over the course of 15 minutes, and the mixture is then left to cool to room temperature.

Example 14

Propylene Oxide Adduct+plasticiser 83 g of a propylene oxide adduct of N,N-bisaminopropyl tallow fatty amine (prepared in known manner from 1 mol of N,N-bisaminopropyl tallow fatty amine with 0.5 mol of propylene oxide) and 17 g of benzyl alcohol are homogenised at room temperature.

Example 15

Ethylene Oxide Adduct+plasticiser 82 g of an ethylene oxide adduct of N,N-bisaminopropyl tallow fatty amine (prepared in known manner from 1 mol of N,N-bisaminopropyl tallow fatty amine with 0.5 mol of ethylene oxide) and 18 g of benzyl alcohol are homogenised at room temperature.

Example 16

Mixed Ethylene Oxide/propylene Oxide Adduct 82 g of a mixed ethylene oxide/propylene oxide adduct of N,N'-bisaminopropyl tallow fatty amine (prepared in known manner from 1 mol of N,N'-bisaminopropyl tallow fatty amine with 0.25 mol of ethylene oxide and 0.25 mol of propylene oxide).

Example 17

Comparison Example

Commercial polyaminoimidazoline, prepared by condensation of triethylenetetramine and tall oil fatty acid according to processes known per se.

Example 18

Comparison Example

Commercial polyaminoimidazoline, prepared by condensation of triethylenetetramine and dimerised fatty acid according to processes known per se.

The properties and measurement results for Examples 1–18 are listed in the following Table 1.

TABLE 1

| | Properties | | | | | |
|---|---|---|---|---|---|---|
| Example/ | 1 | 2 | 3 | 4 | 5 | 6 |
| Viscosity in mPa · s/25° C. | 430 | 480 | 2000 | 750 | 1200 | 370 |
| Amine number mg KOH/g | 335 | 328 | 330 | 332 | 330 | 405 |
| Colour number (Gardner) | 2 | 3 | 4–5 | 2–3 | 2–3 | 1–2 |
| g hardener per 100 g resin *1 | 88 | 92 | 90 | 95 | 100 | 75 |
| Tecam value (min) | 120 | 130 | 57 | 65 | 40 | 47 |
| Example/ | 7 | 8 | 9 | 1 | 1 | 1 |
| Viscosity in mPa · s/25° C. | 1800 | 240 | 67 | 50 | 37 | 45 |
| Amine number mg KOH/g | 300 | 302 | 296 | 365 | 315 | 356 |
| Colour number (Gardner) | 3 | 2 | 1 | <1 | 1 | 1 |
| g hardener per 100 g resin *1 | 105 | 98 | 100 | 80 | 80 | 90 |
| Tecam value (min) | 105 | 82 | 136 | 92 | 65 | 400 |
| Example/ | 1 | 1 | 1 | 1 | 1 | 1 |
| Viscosity in mPa · s/25° C. | 92 | 90 | 185 | 160 | 2100 | 16000 |
| Amine number mg KOH/g | 320 | 328 | 332 | 390 | 390 | 390 |
| Colour number (Gardner) | 1–2 | 1–2 | 1–2 | 8 | 8 | 8 |
| g hardener per 100 g resin *1 | 80 | 77 | 50 | 50 | 50 | 50 |
| Tecam value (min) | 78 | 87 | 180 | 160 | 180 | 120 |
| Development of Shore D hardness at 10° C.: | | | | | | |
| Example/measured values | | | | | | |
| 1 day | 7 | 8 | 0 | 1 | 7 | 5 | 0 | 0 |
| 2 days | 5 | 8 | 6 | 7 | 0 | 7 | 1 | 5 | 0 |
| End hardness *2 | 0 | 8 | 9 | 7 | 8 | 1 | 7 | 8 | 0 |
| Example/measured values | 0 | 1 | 2 | 3 | 4 | 5 | 6 | 7 | 8 |
| 1 day | | 5 | | 5 | 7 | 8 | | | 8 |
| 2 days | 5 | 1 | 0 | 5 | 9 | 0 | 0 | 7 | 9 |
| End hardness *2 | 4 | 7 | 2 | 1 | 2 | 8 | 7 | 8 | 5 |

TABLE 1-continued

| Early water resistance after 24 hours' storage at: | | | | | | | | | |
|---|---|---|---|---|---|---|---|---|---|
| Example/measured values | | | | | | | | | |
| 10° C./80% A. | | | | | | | | | |
| 23° C./50% A. | | | | | | | | | |

| Example/measured values | 0 | 1 | 2 | 3 | 4 | 5 | 6 | 7 | 8 |
|---|---|---|---|---|---|---|---|---|---|
| 10° C./80% A. | | | −2 | −2 | | | | | |
| 23° C./50% A. | | | | | | | | | |

Note:
A. relative atmospheric humidity
*[1]Araldite GY 250 = commercial epoxy resin based on bisphenol A, epoxy equivalent weight: 185;
*[2]curing 2 days at room temperature and 24 hours at 70° C.

What is claimed is:

1. A product comprising one or more compound(s) of formula (I)

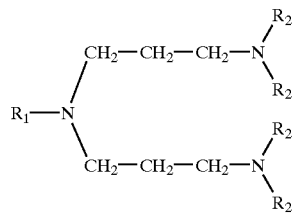

wherein $R_1$ is a hydrocarbon radical having from 8 to 22 carbon atoms, and from 50 to 90 per cent of the $R_2$ radicals of the product denote a hydrogen atom and the remaining $R_2$ radicals of the product denote a group selected from a) a radical of formula

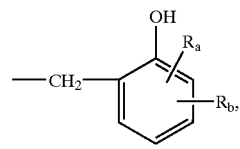

wherein $R_a$ and $R_b$ are each independently of the other a hydrogen atom or an aliphatic, cycloaliphatic, aromatic or araliphatic radical having from 1 to 22 carbon atoms, b) a radical of formula —$CH_2$—$CH(R_c)$—OH, wherein $R_c$ is —H or —$CH_3$, and c) a radical of formula —$CH_2$—$CH_2$—CN.

2. A product according to claim 1, wherein from 60 to 85 per cent, preferably from 65 to 80 percent, of the $R_2$ radicals of the product denote a hydrogen atom.

3. A product according to claim 1 in the form of a compound of formula (I) wherein two or three, preferably three, of the R2 radicals of the product denote a hydrogen atom.

4. A product according to claim 1, wherein $R_1$ is a hydrocarbon radical having from 12 to 22 carbon atoms that is optionally branched and optionally contains multiple bonds.

5. A process comprising reacting one or more products according to claim 1, either alone or in any desired combination, with an epoxy compound.

* * * * *